(12) United States Patent
Matson et al.

(10) Patent No.: US 10,448,955 B2
(45) Date of Patent: Oct. 22, 2019

(54) COMPRESSIBLE INTRAVASCULAR EMBOLIZATION PARTICLES AND RELATED METHODS AND DELIVERY SYSTEMS

(71) Applicant: Biosphere Medical, Inc., South Jordan, UT (US)

(72) Inventors: Louis R. Matson, Pollock Pines, CA (US); Gerald R. McNamara, Reno, NV (US); Donald K. Brandom, Davis, CA (US)

(73) Assignee: BIOSPHERE MEDICAL, INC., South Jordan, UT (US)

( * ) Notice: Subject to any disclaimer, the term of this patent is extended or adjusted under 35 U.S.C. 154(b) by 251 days.

(21) Appl. No.: 13/717,452

(22) Filed: Dec. 17, 2012

(65) Prior Publication Data

US 2013/0190795 A1 Jul. 25, 2013

Related U.S. Application Data

(62) Division of application No. 11/669,119, filed on Jan. 30, 2007, now abandoned.
(Continued)

(51) Int. Cl.
*A61B 17/12* (2006.01)
*A61L 24/00* (2006.01)
*A61L 24/06* (2006.01)

(52) U.S. Cl.
CPC ...... *A61B 17/1219* (2013.01); *A61L 24/0036* (2013.01); *A61L 24/06* (2013.01); *A61L 2430/36* (2013.01)

(58) Field of Classification Search
CPC .. A61L 24/0036; A61L 2430/36; A61L 24/06; A61B 17/1219; A61B 17/12181;
(Continued)

(56) References Cited

U.S. PATENT DOCUMENTS 2,659,935 A 11/1953 Hammon
3,673,125 A 6/1972 Takahashi et al.
(Continued)

FOREIGN PATENT DOCUMENTS

EP 0256293 2/1988
EP 0448391 9/1991
(Continued)

OTHER PUBLICATIONS

Finch, 'Polyvinyl Alcohol: Properties and Applications', Chapter 17, pp. 427-460, 1973.
(Continued)

*Primary Examiner* — Eric J Rosen
*Assistant Examiner* — Chima U Igboko
(74) *Attorney, Agent, or Firm* — Stoel Rives LLP

(57) ABSTRACT

The present invention relates to substantially compressible, spherical porous embolization particles, including methods of making and using the particles. Methods of using the particles include methods of embolization, in which at least one particle can be positioned in a target area of a blood vessel. The particles can also include interior pores that extend to the surface of the particles. Further, the invention relates to embolization delivery systems for the introduction of the particle into the vascular luer.

18 Claims, 8 Drawing Sheets

Related U.S. Application Data

(60) Provisional application No. 60/764,825, filed on Jan. 30, 2006.

(58) Field of Classification Search
CPC ...... A61K 9/14; A61K 9/0024; A61K 9/5094; A61K 9/51; A61K 51/1241; A61K 51/1244; A61K 51/1251; A61K 51/1255; A61K 51/1258; C08L 29/04
USPC .......................................... 606/191; 424/489
See application file for complete search history.

(56) References Cited

U.S. PATENT DOCUMENTS

| | | | |
|---|---|---|---|
| 3,919,411 A | 11/1975 | Glass et al. | |
| 4,090,010 A | 5/1978 | Warwicker | |
| 4,268,495 A | 5/1981 | Muxfeldt et al. | |
| 4,306,031 A | 12/1981 | Itagaki et al. | |
| 4,314,032 A | 2/1982 | Murrayama et al. | |
| 4,320,040 A | 3/1982 | Fujita et al. | |
| 4,350,773 A | 9/1982 | Itagaki et al. | |
| 4,367,323 A | 1/1983 | Kitamura et al. | |
| 4,657,553 A | 4/1987 | Taylor | |
| 4,680,171 A | 7/1987 | Shell | |
| 4,803,075 A | 2/1989 | Wallace et al. | |
| 4,863,972 A | 9/1989 | Itagaki et al. | |
| 4,999,188 A | 3/1991 | Solodovnik et al. | |
| 5,007,940 A | 4/1991 | Berg | |
| 5,028,332 A | 7/1991 | Ohnishi | |
| 5,092,883 A | 3/1992 | Epply et al. | |
| 5,106,876 A | 4/1992 | Kawamura | |
| 5,114,577 A | 5/1992 | Kusano et al. | |
| 5,116,387 A | 5/1992 | Berg | |
| 5,158,573 A | 10/1992 | Berg | |
| 5,186,922 A | 2/1993 | Shell et al. | |
| 5,202,352 A | 4/1993 | Okada et al. | |
| 5,258,042 A | 11/1993 | Mehta | |
| 5,336,263 A | 8/1994 | Ersek | |
| 5,403,870 A | 4/1995 | Gross | |
| 5,410,016 A | 4/1995 | Hubbell et al. | |
| 5,470,911 A | 11/1995 | Rhee et al. | |
| 5,550,188 A | 8/1996 | Rhee et al. | |
| 5,554,659 A | 9/1996 | Rosenblatt | |
| 5,571,182 A | 11/1996 | Ersek et al. | |
| 5,578,709 A | 11/1996 | Woiszwillo | |
| 5,583,162 A | 12/1996 | Li et al. | |
| 5,593,990 A | 1/1997 | D'Amato | |
| 5,624,685 A | 4/1997 | Takahashi et al. | |
| 5,629,327 A | 5/1997 | D'Amato | |
| 5,635,215 A | 6/1997 | Boschetti et al. | |
| 5,648,100 A | 7/1997 | Boschetti et al. | |
| 5,653,922 A | 8/1997 | Li et al. | |
| 5,712,291 A | 1/1998 | D'Amato | |
| 5,752,974 A | 5/1998 | Rhee et al. | |
| 5,760,097 A | 6/1998 | Li et al. | |
| 5,785,977 A | 7/1998 | Briethbarth | |
| 5,798,096 A | 8/1998 | Pavlyk | |
| 5,823,198 A | 10/1998 | Jones et al. | |
| 5,853,698 A | 12/1998 | Straub et al. | |
| 5,863,957 A | 1/1999 | Li et al. | |
| 5,891,470 A | 4/1999 | Rinaldi et al. | |
| 5,895,411 A | 4/1999 | Irie | |
| 5,925,683 A | 7/1999 | Park | |
| 5,955,108 A | 9/1999 | Sutton et al. | |
| 5,964,806 A | 10/1999 | Cook et al. | |
| 6,048,908 A | 4/2000 | Kitagawa et al. | |
| 6,060,530 A | 5/2000 | Chaouk et al. | |
| 6,060,582 A | 5/2000 | Hubbell et al. | |
| 6,099,952 A | 8/2000 | Cercone | |
| 6,100,306 A | 8/2000 | Li et al. | |
| 6,139,963 A | 10/2000 | Fujii et al. | |
| 6,160,025 A | 12/2000 | Slaikeu | |
| 6,165,193 A | 12/2000 | Greene, Jr. et al. | |
| 6,191,193 B1 | 2/2001 | Lee et al. | |
| 6,218,440 B1 | 4/2001 | Kitagawa et al. | |
| 6,242,512 B1 | 6/2001 | Figge et al. | |
| 6,306,922 B1 | 10/2001 | Hubbell et al. | |
| 6,315,762 B1* | 11/2001 | Recinella et al. | 604/247 |
| 6,335,028 B1 | 1/2002 | Vogel | |
| 6,337,198 B1 | 1/2002 | Levene et al. | |
| 6,436,424 B1 | 8/2002 | Vogel | |
| 6,488,952 B1 | 12/2002 | Kennedy et al. | |
| 6,500,190 B2 | 12/2002 | Greene, Jr. et al. | |
| 6,537,569 B2 | 3/2003 | Cruise | |
| 6,565,885 B1 | 5/2003 | Tarara et al. | |
| 6,602,975 B2 | 8/2003 | Hubbell et al. | |
| 6,652,883 B2 | 11/2003 | Goupil et al. | |
| 6,660,301 B1 | 12/2003 | Vogel | |
| 6,676,971 B2 | 1/2004 | Goupil et al. | |
| 6,680,046 B1 | 1/2004 | Boschetti | |
| 6,710,126 B1 | 2/2004 | Hirt et al. | |
| 6,790,456 B2 | 9/2004 | Vogel | |
| 6,911,219 B2 | 6/2005 | Matson | |
| 7,060,298 B2 | 6/2006 | Vogel | |
| 7,338,657 B2 | 3/2008 | Vogel | |
| 7,588,780 B2 | 9/2009 | Buiser et al. | |
| 7,591,993 B2 | 9/2009 | Boschetti | |
| 7,780,645 B2 | 8/2010 | Jones | |
| 7,837,733 B2 | 11/2010 | Collins et al. | |
| 7,901,770 B2 | 3/2011 | DiCarlo et al. | |
| 2003/0059371 A1* | 3/2003 | Matson et al. | 424/9.3 |
| 2003/0185895 A1 | 10/2003 | Lanphere et al. | |
| 2003/0185896 A1 | 10/2003 | Busier et al. | |
| 2003/0203985 A1 | 10/2003 | Baldwin | |
| 2003/0206864 A1 | 11/2003 | Mangin | |
| 2003/0211165 A1 | 11/2003 | Vogel | |
| 2003/0215519 A1 | 11/2003 | Schwarz et al. | |
| 2003/0232895 A1 | 12/2003 | Omidian et al. | |
| 2003/0233150 A1* | 12/2003 | Bourne et al. | 623/23.72 |
| 2004/0037887 A1* | 2/2004 | Boume | A61L 27/16 424/486 |
| 2004/0068039 A1 | 4/2004 | Lyoo et al. | |
| 2004/0076582 A1* | 4/2004 | Dimatteo | A61K 9/1635 424/1.49 |
| 2004/0091425 A1 | 5/2004 | Boschetti | |
| 2004/0091543 A1 | 5/2004 | Bell et al. | |
| 2004/0092883 A1 | 5/2004 | Casey et al. | |
| 2004/0096514 A1 | 5/2004 | Vogel | |
| 2004/0096662 A1* | 5/2004 | Lanphere et al. | 428/402 |
| 2004/0101564 A1* | 5/2004 | Rioux et al. | 424/488 |
| 2004/0220611 A1* | 11/2004 | Ogle | 606/200 |
| 2005/0025708 A1 | 2/2005 | Vogel | |
| 2005/0043585 A1 | 2/2005 | Datta et al. | |
| 2005/0085847 A1 | 4/2005 | Galdonik et al. | |
| 2005/0095428 A1 | 5/2005 | Dicarlo et al. | |
| 2005/0119687 A1 | 6/2005 | Dacey et al. | |
| 2005/0158393 A1 | 7/2005 | Reb | |
| 2006/0009851 A1* | 1/2006 | Collins et al. | 623/17.16 |
| 2006/0052816 A1 | 3/2006 | Bates et al. | |
| 2006/0063732 A1 | 3/2006 | Vogel | |
| 2006/0069168 A1 | 3/2006 | Tabata et al. | |
| 2006/0178696 A1* | 8/2006 | Porter | A61B 17/12 606/200 |
| 2006/0251582 A1 | 11/2006 | Reb | |
| 2007/0005094 A1 | 1/2007 | Eaton et al. | |
| 2008/0033366 A1 | 2/2008 | Matson | |
| 2008/0039890 A1 | 2/2008 | Matson | |
| 2008/0118569 A1 | 5/2008 | Vogel | |
| 2008/0208171 A1 | 8/2008 | Argenta et al. | |
| 2008/0220077 A1 | 9/2008 | Vogel | |
| 2008/0268367 A1 | 10/2008 | Nair | |
| 2009/0092676 A1 | 4/2009 | Richard et al. | |
| 2009/0117196 A1 | 5/2009 | Boschetti | |
| 2009/0186094 A1 | 7/2009 | Vogel | |
| 2010/0119572 A1 | 5/2010 | Boschetti | |
| 2010/0222802 A1 | 9/2010 | Gillespie et al. | |
| 2011/0182998 A1 | 7/2011 | Reb et al. | |
| 2011/0033508 A1 | 9/2011 | Vogel et al. | |
| 2011/0212179 A1 | 9/2011 | Liu | |

FOREIGN PATENT DOCUMENTS

| | | |
|---|---|---|
| EP | 0470569 | 2/1992 |
| EP | 1128816 | 9/2001 |

(56) References Cited

FOREIGN PATENT DOCUMENTS

| | | |
|---|---|---|
| EP | 0764047 | 8/2003 |
| EP | 0993337 | 4/2004 |
| JP | 49108168 | 10/1974 |
| JP | 53050290 | 5/1978 |
| JP | 57128709 | 8/1982 |
| JP | 4036328 | 2/1992 |
| JP | 5294839 | 11/1993 |
| JP | 6056676 | 3/1994 |
| WO | WO 99/11196 | 3/1993 |
| WO | WO 97/27888 | 8/1997 |
| WO | WO 98/04198 | 2/1998 |
| WO | WO 98/16265 | 4/1998 |
| WO | WO 1999/00187 | 1/1999 |
| WO | WO 99/12577 | 3/1999 |
| WO | 200023054 | 4/2000 |
| WO | WO 2000/23054 | 4/2000 |
| WO | WO 01/68720 | 9/2001 |
| WO | WO 02/034300 | 5/2002 |
| WO | WO 03/084582 | 10/2003 |
| WO | WO 2004/007597 | 1/2004 |
| WO | 2004071495 | 8/2004 |
| WO | WO 04/071495 | 8/2004 |
| WO | WO 06/046155 | 5/2006 |
| WO | WO 2007/090127 | 8/2007 |
| WO | WO 2007/090130 | 8/2007 |
| WO | WO 2008/014060 | 1/2008 |
| WO | WO 2008/041001 | 4/2008 |
| WO | WO 2010/062678 | 6/2010 |

OTHER PUBLICATIONS

Brown et al., 'Synthese et Copolymerisation de Nouveauz Monomeres Acryliques Diiodes et Triiodes', Bulletin de la Societe Chimique de France, Jul.-Aug. 1986, pp. 669-677, with English summary.
Olson, M.D., 'Angiogenesis Research Enjoys Growth Spurt in the 1990's', Journal of the National Cancer Institute, vol. 88, No. 12, Jun. 19, 1996, pp. 786-787.
Hori et al., 'A Study of Development and Practical Uses of a New MRI Machine', Innervision 1998, pp. 15-30, with English summary.
Osuga et al. 'A New Embolic Material: SAP Microsphere', Japanese Journal of Clinical Medicaine, pp. 534-538, 2001, with English summary.
Kim et al., 'Gas Foamed Open Porous Bipdegradable Polymeric Microspheres', 2006 (available online Jul. 2005), Elsevier, Biomaterials, vol. 27, pp. 152-159.
Merriam-Webster® Online Dictionary entry for 'pore' retrieved from <www-merriam-webster.com> on Mar. 19, 2011, p. 1.
Bachtsi et al., 'An Experimental Investigation of Enzyme Release from Poly(vinyl alcohol) Crosslinked Microspheres', J Microencapsulation 12(1): 23-35, 1995.
Barnes et al., 'Fluorescence Imaging of Single Molecules in Polymer Microspheres', Cytometry 36: 169-175, 1999.
Barr et al., 'Polyvinyl alcohol foam Particle Sizes and Concentrations Injectable through Microcatheters', JVIR 9(1): 113-118, 1998.
Barton et al., 'Embolizatio of Bone Metastases', J Vasc Intery Radiol 7: 81-88, 1996.
Beese et al., 'Renal Angiography Using Carbon Dioxide', British Journal of Radiology 73: 3-6, 2000.
Benson, 'Highly Porous Polymers', American Laboratory, May 2003, available at http://www.sunstorm-research.com/PDF%20files/Pourous%20Polymers%202003.pdf last visited Nov. 9, 2010.
Benson, 'Cavilink™ Drug Delivery Technology', 2009, available at http://www.polygenetics.com/PDF%20Files/Drug%20Delivery%20Monograph%202008.pdf Last visited Nov. 9, 2010.
Boschetti, 'Polyacrylamide Derivatives to the Service of Bioseparations', J Biochem Biophys Meth 19:21-36, 1989.
Chawla, 'In Vivo Magnetic Resonance Vascular Imaging Using Laser-Polarized 3He Microbubbles', Proc Nat Acad Sci USA 95, 10832-10835, 1998.
Chawla, 'Hyperpolarized Gas as a Vascular Contrast Agent', Center for In vivo Microscopy. Located at http://www.civm.mc.duke,edu/civmProjectsIHPcontrastIHPContrast.html> visited on Jul. 25, 2002.
Derdeyn et al., 'Polyvinyl Alcohol Particle Size and Suspension Characteristics', American Journal of Neuroradiology 16: 1335-1343, 1995.
Dunn, 'The Peculiarities of Polyvinyl Alcohol', Chemistry & Industry, London, pp. 801-806, 1980.
Flandroy et al., 'Clinical Applications of Microspheres in Embolization and Chemoembolization: A Comprehensive Review and Perspectives', In: Pharmaceutical Particulate Carriers in Medical Applications, Rolland, A. Ed, New York: Marcel Dekker, Inc., 61: 321-366, 1993.
Herrmann et al., 'Uber den Poly-vinylalkohol', Berichte 60:1658-1663, 1927.
Hori et al., 'A New Embolic Material: Superabsorbent Polymer Microsphere and Its Embolic Effects', J International Radiol 11(3): 75-81, 1996.
Hori et al., 'An Experimental Study of a New Embolic Material-Lipiodol Suspension of Water-Absorbent Particle', Nippon Acta Radiologica 53(1): 50-56, 1993.
Hori et al., 'Embolotherapy of Large Hepatocellular Carcinoma Using a New, Permanent, Spherical Embolic Material Without Anti-Neoplastic Agents', Cardiovasc Intervent Radiol 24 (Suppl 1) S203, 2001.
Hori et al., 'Vessel Embolic Materials,' Intervent Radiol 33: 109-112, 1999.
Inoue et al., 'Experimental Studies of Segmental Hepatic Artery Embolization with a Super Absorbent Embolic Agent', Nippon Acta Radiplogica 50: 1439-1441, 1990.
Iwase et al., 'Hand-Assisted Laparoscopic Splenectomy for Idiopathis Thrombocytopenic Purpura During Pregnancy', Surgical Laparoscopy, Endoscopy & Percutaneous Techniques 11(1): 532-56, 2001.
Iwase et al., 'Laparoscopically Assisted Splenectomy Following Preoperative Splenic Artery Embolization Using Contour Emboli for Myelofibrosis with Massive Splenomegaly', Surgical Laparoscopy, Endoscopy & Percutaneous Techniques 12(5): 197-202, 1999.
Iwase et al., 'Splenic Artery Embolization Using Contour Emboli Before Laparoscopic or Laparoscopically Assisted Splenectomy', Surgical Laparoscopy, Endoscopy & Percutaneous Techniques 12(5): 331-336, 2002.
Jiaqi, 'A New Embolic Material: Super Absorbetn Polymer (SAP) Microsphere and Its Embolic Effects', Nippon Acta Radiplogica 56(1): 19-24, 1996.
Khankan et al., 'Embolic Effects of Superabsorbent Polymer Microspheres in Rabbit Renal Model: Comparison with Trisacryl Gelatin Microspheres and Polyvinyl Alcohol', Radiat Med 22(6): 384-390, 2004.
Kimura et al., 'Transcaterterial Embolization of AVM in Pancreas', Japanese J Clin Radiol 43: 311-314, 1998.
Kitamura et al., 'Polymer with a High Water Absorption Property—Sumika Gel', Sumitomo Chemical Special Issue 1-9, 1980.
Kusano et al., Low-Dose Particulate Polyvinylalcohol Embolization in Massive Small Artery Intestinal Hemorrhage: Experimental and Clinical Results', Investigative Radiology 22: 388-392, 1987.
Lee et al., 'Polysterene Macroporous Bead Support for Mammalian Cell Culture', Bipchen Eng VII (eds. D. Dibiasion and R. Mutharason) Ann NY Acad of Sci 665: 137-145, 1992.
Mandai et al., 'Direct Thrombosis of Aneurysms with Cellulose Acetate Polymer. Part I: Results of Thrombosis in Experimental Aneurysms', J Neurosurgery 77: 497-500, 1992.
Marvel et al., 'End Group Structure of Polyvinyl Alcohol', The Journal of the American Chemical Society 65: 1710, 1943.
Marvel et al., 'The Structure of Vinyl Polymers. II: Polyvinly Alcohol', The Journal of the American Chemical Society 60: 1045, 1938.
Mavligit et al., 'Gastrointestinal Leiomyosarcoma Metastatic to the Liver', Cancer 75(8): 2083-2088, 1995.
Motohashi et al., 'Superabsorbent Sumikagel®', Sumitomo Chemistry 35-47, 1985.

(56) References Cited

OTHER PUBLICATIONS

Muller-Schulte et al., 'Novel Magnetic Microspheres on the Basis of Poly(vinly alcohol) as Affinity Medium for Quantitative Detection of Glycated Haemoglobin', J Chromatography A 711: 53-60, 1995.
Norrby et al., 'Angiogenesis: New Aspects Relating to Its Initiation and Control', APMIS 105: 417-437, 1997.
Leeds, 'Vinyl Polymers (Alcohol)', Encyclopedia of Chemical Technology, Kirkothmer ed., 21: 353-368, Wiley-Interscience, New York, 2nd ed., 1970.
McDowell et al., 'Some Relationships Between Polyvinly Acetates and Polyvinly Alcohols', J Am Soc 62: 415, 1940.
Novak, 'Embolization Materials', In Interventional Radiology, Dondelinger, R.F. et al., eds., Thieme Medical Publishers, NY, pp. 295-313, 1990.
O'Reilly, 'The Preclinical Evaluatin of Angiogenesis Inhibitors', Investigational New Drugs 15: 5-13, 1997.
Osuga et al., 'Management of Advanced Pelvic Bone Tumors by Transarterial Embolotherapy Using SAP-Microspheres: A Preliminary Report', Cardiovascular Intervent Radiol 22: S130, 1999.
Osuga et al., Embolization of High Flow Arteripvenous Malformations: Experience wih Use of Superabsorbent Polymer Microspheres, J Vasc Intervent Radiol 13(11): 1125-1133, 2002.
Osuga et al., 'Transarterial Embolization for Large Hepatocellular Carcinoma with Use of Superabsorbent Polymer Microspheres: Initial Experience', J Vasc Intervent Radiol 13(9 pt 1): 929-934, 2002.
Repa et al., 'Mortalities Associated with Use of a Commercial Suspension of Polyvinyl Alcohol', Radiology 170(2): 395-399, 1989.
Rump et al., 'Pharmacokinetics of Intraarterial Mitomycin C in the Chemoembolisation Treatment of Liver Metastases', Gen Pharmac 27(4): 669-671, 1996.
Staudinger et al., 'Uber Poly-Vinylacetat Und Poly-Vinylalkohol', Berichte 60: 1782 (with English abstract), 1927.
Staudinger, 'Uber die Konstitution von Hockpolymeren Kunststoffen', Journal fur Praktische Chemie N.F. 155: 261 (with English abstract), 1940.
Sugawara et al., 'Experimental Investigations Concerning a New Liquid Embolization Method: Combined Administration of Ethanol-Estrogen and Polyvinly Acetate', Neuro Med Chir (Tokyo) 33: 71-76, 1993.
Taki et al., 'A New Liquid Material for Embolization of Arteriovenous Malformations', AJNR 11: 163-168, 1990.
Thanoo et al., 'Preparation and Properties of Barium Sulphate and Methyl Lothalamate Loaded Poly(vinly alcohol) Microspheres as Parippques Particulate Emboli', J Applied Biomaterials 2: 67-72, 1991.
Thanoo et al., 'Controlled Release of Oral Drugs from Cross-Linked Polyvinyl alcohol Microspheres', J Pharm Pharmacol 45: 16-20, 1993.
Tao et al., 'Study on Microspheres for Embolization of Hepatic Artery', Acta Pharmaceutice Sinica 23(1): 55-60, (with English translation), 1988.
Vinters et al., 'The Histotoxicity of Cyanoacrylates: A Selective Review', Neuroradiology 27: 279-291, 1985.
Wakhloo et al., 'Extended Preoperative Polyvinly Alcohol Microembolization of Intracranial Meningiomas: Assessment of Two Embolization Techniques', American Journal of Neurology 14: 571-582, 1993.
Wang et al., 'Porous Poly (lactic-co-glycolide) Microsphere Sintered Seaffolds for Tissue Repair Applications', Material Science and Engineering 29: 2502-2507, 2009.
Ziegler et al., 'Angiogenesis Research Enjoys Growth Spurt in 1990's', Journal of the National Cancer Institute 88(12): 786-787, 1996.
Zou et al., 'Experimental Canine Hepatic Artery Embolizaiton with Polyvinyl Alcohol Microsphere', Zhonghua Fang She Xue Za Zhi, Chin J. Radiol, 23(6): 330-332 (with English translation), 1989.
Interview Summary dated Nov. 20, 2006 for U.S. Appl. No. 10/692,785.
Notice of Allowance dated Sep. 29, 2008 for U.S. Appl. No. 12/348,867.
Notice of Allowance and Interview Summary dated Dec. 7, 2009 for U.S. Appl. No. 12/348,867.
International Search Report dated Aug. 21, 2008 for WO2007/090130.
International Search Report dated Aug. 21, 2008 for WO2007/090127.
Lewis et al., 'Comparative in Vitro Evaluation of Microspherical Embolization Agents', J Mater Sci: Mater Med 17: 1193-1204, 2006.
Kim et al., 'Biodegradable Polymeric Microspheres with 'Open/Closed' Pores for Sustained Release of Human Growth Hormone', elsevier, Journal of controlled Release, vol. 112, pp. 167-174, 2006.
Schwarz et al., 'Transcatheter Embolization Using Degradable Crosslinked Hydrogels', Elsevier, Biomaterials, vol. 25, pp. 5209-5215, 2004.
Schmedlen et al., 'Photocrosslinkable Polyvinyl Alcohol Hydrogels that can be Modified with Cell Adhesion Peptides for use in Tissue Engineering', Elseiver, Biomaterials, vol. 23, pp. 4325-4332, 2002.
Marra, 'Bone Tissue Engineering,' Hillinger et al., eds., CRC Press; Chapter 6, 'Biodegradable Polymers and Microspheres in Tissue Engineering' p. 1-27, 2005.
Office Action dated Mar. 25, 2011 for U.S. Appl. No. 11/669,127.
Office Action dated May 12, 2010 for U.S. Appl. No. 11/669,127.
Restriction Requirement dated Dec. 29, 2009 for U.S. Appl. No. 11/669,127.
Hori et al., 'Study on the Effect of Arterial Embolization withSuper-Absorbent Polymer', Intervent Radiol 11: 1-11 (with English translation), 1996.
Restriction Requirement dated Dec. 23, 2009 for U.S. Appl. No. 11/669,119.
Office Action dated Dec. 22, 2010 for U.S. Appl. No. 11/669,119.
Office Action dated Apr. 26, 2011 for U.S. Appl. No. 11/669,119.
Office Action dated Aug. 18, 2011 for U.S. Appl. No. 11/669,119.
Office Action dated Apr. 27, 2012 for U.S. Appl. No. 11/669,119.
Laurent et al., 'Trisacryl Gelatin Microspheres for Therapeutic Embolization. I: Development and In Vitro Evaluation', Am J Neuroradiol 17: 533-540, 1996.
Rosenburg 'Protein Analysis and Purification: Benchtop Techniques', Published by Birkhauser, Boston MA USA. Protocol 10.1, pp. 330-331, 2005.
Aguilar, 'Methods in Molecular Biology: HPLC of Peptides and Proteins Methods and Protocols', Humana Press Inc. vol. 251, p. 67, 2004.
Dunn et al. 'Methods in Molecular Biology: Peptide Synthesis Protocols', 36:5, 1994.
Zimmerman et al., 'Renal Pathology After Arterial Yttrium-90 Microsphere Administration in Pigs: A Model for Superselective Radioembolization Therapy', Invest Radiol, vol. 30, No. 12, pp. 716-723, 1995.
Poon et la., 'A Phase I/II Trial of Chemoembolization for Hepatocellular Carcinoma Using a Novel Intra-Arterial Drug-Arterial Drug-Eluting Bead', Clinical Gastroenterology and Hepatology, vol. 5, pp. 1100-1108, 2007.
Declaration of Dr. Andrew Lennard Lewis, Director of Research and Development, Biocompatibles UK Limited, May 16, 2012.
Desai, 'Downstream Processing of Proteins: Methods and Protocols', Methods in Biotechnology, Humana Press vol. 9, 2000.
Office Action dated Sep. 17, 2012 for U.S. Appl. No. 11/669,119.
Restriction Requirement dated Nov. 29, 2012 for U.S. Appl. No. 13/126,456.
Blaker et al., 'Novel Fabrication Techniques to Produce Microspheres by Thermally Induced Phase Separation for Tissue Engineering and Drug Delivery', Acta Biomaterialia vol. 4, Issue 2, p. 264, Mar. 2008.
Office Action dated Jul. 18, 2013 for U.S. Appl. No. 13/126,456.
Office Action dated Dec. 18, 2013 for U.S. Appl. No. 11/669,127.
Precision Bead Marketing Brochure, 2005, 4 pgs.
Invoice to Pacific Medical (HK) Co., Ltd., Dec. 5, 2005, 1 pg.

(56) References Cited

OTHER PUBLICATIONS

Lin et al., 'Microarchitetural and Mechanical Characterisation of Oriented Polymer Scaffolds', Biomaterials 24, p. 481-489, 2003.
Tuan et al., 'Application of Microp CT and Computation Modeling in Bone Tissue Engineering', Computer-Aided Design 37, p. 1151-1161, 2005.
Protocol 10.1 Preparation of the Gel: Hydrating and Degassing, Chapter 10 Chromatography, 330-331, no date available.
Bollag, 'Gel-Filtration Chromatography', Methods in Molecular Biology, vol. 36: Peptide Analysis Protocols, 1994.
Jayakrishnan et al., 'Microspheres for Endovascular Embolization', Microspheres, Microcapsules and Liposomes vol. 2, Medical and Biptechnology Applications, R. Arshady, Ed., Citus Books, London, 1999, pp. 97-126.
Opposition to EP1986706B1: Facts and Arguments dated May 17, 2012.
Response to Opposition dated Mar. 8, 2013 for EP1986706.
EPO Preliminary Opinion dated Apr. 12, 2013 for EP1986706.
Opponent Submission dated Aug. 13, 2013 for EP1986706.
Patentee Submission dated Aug. 29, 2013 for EP1986706.
Statement of Grounds of Appeal dated Mar. 18, 2014 for EP1986706.
Decision Revoking European Patent dated Nov. 8, 2013 for EP1986706.
Grounds for Decision of Opposition dated Nov. 8, 2013 for EP1986706.
Letter Regarding Opposition Procedure dated Sep. 27, 2013 for EP1986706.
Letter Regarding Opposition Procedure dated Aug. 29, 2013 for EP1986706.
Letter Regarding Opposition Procedure dated Aug. 13, 2013 for EP1986706.
Office Action dated Aug. 15, 2014 for U.S. Appl. No. 11/669,127.
Gulbekian et al., 'Polyvinyl Alcohol in Emulsion Polymerization', Chapter 17, pp. 427-460.
Notice of Allowance dated Dec. 7, 2009 for U.S. Appl. No. 12/348,867.
Office Action dated Sep. 21, 2015 for U.S. Appl. No. 11/669,127.
Office Action dated Dec. 26, 2014 for U.S. Appl. No. 13/717,452.
Toyoshima, 'Moulded Products From Polyvinyl Alcohol', Chapter 20, pp. 523-528, 1973.
Notice of Allowance dated Feb. 18, 2005 for U.S. Appl. No. 10/133,177.
Notice of Allowance dated Jul. 25, 2003 for U.S. Appl. No. 09/419,114.
Notice of Allowance dated Sep. 29, 2008 for U.S. Appl. No. 10/692,785.
Office Action dated Jan. 24, 2008 for U.S. Appl. No. 10/692,785.
Office Action dated May 6, 2016 for U.S. Appl. No. 11/669,127.
Office Action dated Jun. 2, 2006 for U.S. Appl. No. 10/692,785.
Office Action dated Jul. 3, 2002 for U.S. Appl. No. 09/419,114.
Office Action dated Jul. 12, 2007 for U.S. Appl. No. 10/692,785.
Office Action dated Jul. 23, 2009 for U.S. Appl. No. 12/348,867.
Office Action dated Aug. 2, 2004 for U.S. Appl. No. 10/133,177.
Office Action dated Sep. 4, 2008 for U.S. Appl. No. 10/692,785.
Office Action dated Oct. 30, 2001 for U.S. Appl. No. 09/419,114.
Office Action dated Oct. 30, 2006 for U.S. Appl. No. 10/692,785.
Office Action dated Nov. 16, 2005 for U.S. Appl. No. 10/692,785.
Hori, et al., "Study on the Effect of Arterial Embolization with Super-Absorbent Polymer", Intervent Radiol, 11, with English Translation, 1996, 1-11.
Office Action dated Nov. 15, 2016 for U.S. Appl. No. 11/669,127.
Office Action dated Jul. 6, 2017 for U.S. Appl. No. 11/669,127.
Office Action dated Nov. 14, 2018 for U.S. Appl. No. 11/669,127.
Advanced Meditech International: What is PVA?, www.ameditech.com, retrieved Oct. 12, 2018.

* cited by examiner

COMPRESSIBLE INTRAVASCULAR EMBOLIZATION PARTICLES AND RELATED METHODS AND DELIVERY SYSTEMS

CROSS-REFERENCE TO RELATED APPLICATIONS

This patent application is a divisional of now pending U.S. patent application Ser. No. 11/669,119, entitled COMPRESSIBLE INTRAVASCULAR EMBOLIZATION PARTICLES AND RELATED METHODS AND DELIVERY SYSTEMS, filed on Jan. 30, 2007, which claims the benefit of U.S. Patent Application No. 60/764,825, filed on Jan. 30, 2006, each of which is fully incorporated by reference herein.

FIELD OF THE INVENTION

The present invention relates to compressible embolization particles, including supplemental embolization particles, methods of making and using the particles, and delivery systems for delivery of the particles.

BACKGROUND OF THE INVENTION

Some intravascular interventional procedures produce an artificial embolism in mammals that is useful in controlling internal bleeding, blocking the blood supply to tumors, or relieving pressure in a vessel wall near an aneurysm. Known methods for producing an artificial embolism include use of (1) inflatable and detachable balloons, (2) coagulating substances, (3) later-curing polymeric substances, (4) occlusive wire coils, (5) embolization particles, and (5) supplemental occlusive embolic materials. Disadvantages relating to the known methods include recanalization, perforation of blood vessels, inadvertent downstream embolization due to fragmentation or release of trapped particles, poor positioning control, instability, imprecise sizing, and shrinkage or movement of the embolic material.

Early embolization particles were made by chopping or grinding polyvinyl alcohol (PVA) foam or sponge. Such PVA foam or sponge embolization particles are irregularly shaped and generally contain a range of pore sizes that are produced during the manufacturing process by whipping air into the PVA solution prior to crosslinking. Disadvantages of these particles include their non-precise size (aspect ratios) and open edges on the particles that cause them to clump together and subsequently plug up delivery catheters.

Spherical particles minimize these disadvantages. In addition, spherical particles can penetrate deeper into the vasculature than traditional particles due to the uniform shape of the particle. Existing spherical embolics include Biocompatibles International plc's Bead Block™ Biosphere Medical, Inc.'s Embosphere™ and Boston Scientific Corporation's Contour SE™. The Bead Block™ product is a PVA gel and does not have macropores (that is, the pores are less than 1 micron in diameter). Embosphere™ is a gel made of an acrylic co-polymer (trisacryl) and does not have macropores. Contour SE™ is made of PVA has an onion shape but has no surface macropores.

However, spherical embolization particles have several disadvantages. For example, the smooth surface of these particles may affect the stable integration of such particles within the occlusive mass comprising the particles, clotted blood and ultimately fibrous tissue. In addition, the compression of such particles is only about 20-35% in one dimension thereby limiting the size of the embolization particle that can be used in a given catheter.

SUMMARY OF THE INVENTION

The invention includes compressible substantially spherical, porous embolization particles. The interior porous extend to the particle surface to form an exterior layer having exterior pores. The compressible embolization particle preferably has a diameter from about 1,000 to 10,000 microns or more in its hydrated, fully expanded state. The particles can be compressed in one dimension to at least 50% of the diameter of the fully extended particle and in some cases can be compressed to 5% of the original diameter.

The compressible embolization particle is preferably radiopaque. In a preferred embodiment, the compressible embolization particle is made of a crosslinked polyvinyl alcohol ("PVA") polymer. In some embodiments, the embolization particle also has an annular porous ring around the spherical particle which is generated during particle formation.

The invention also includes an artificial embolization kit. The kit has one or more compressible embolization particle as described herein and a delivery device. The delivery device has a connection component and two syringes. The connection component is adapted to connect with the two syringes and to control the flow of fluid in the delivery device.

The invention includes an embolization device comprising a compressible embolization particle(s) and a delivery system such as a catheter. In some embodiments, the embolization device contains the particle in the lumen of the catheter.

The invention also includes a method of embolization where a percutaneous delivery system containing a compressible embolization particle is positioned so that the delivery system is in proximity to a target region of a blood vessel. The particle is compressed in the lumen of the delivery system and has a cross-sectional diameter that corresponds to the diameter of the lumen. The compressed embolization particle is then ejected from the delivery system by pressure or the use of a blunt ended guidewire so that the particle is initially positioned in the target region. During or after ejection, the particle expands. The diameter of the uncompressed hydrated embolization particle is preferably chosen so that after expansion, the particle attains an expanded state that creates pressure against the interior surface of the vascular wall. The embolization particle therefore conforms to the cross section of the blood vessel.

The invention also includes a method of loading an embolization particle into a catheter. In this method an embolization particle is positioned in a luer hub of a catheter. A syringe containing hydration fluid is coupled to the luer hub and operated to urge the embolization particle out of the luer hub and into the catheter. The syringe is then removed. The particle is then urged through the catheter and into a target area of a patient with a guidewire.

In another embodiment, the invention includes a method of loading an embolization particle into a catheter where an embolization particle is positioned in a luer hub of a catheter. A stopcock is connected to the luer hub and first and second syringes are connected to the stopcock, at least one syringe initially containing hydration fluid. The first syringe is operated to urge the embolization particle out of the luer hub and into the catheter. The second syringe is operated to urge the particle through the catheter.

In another embodiment, the invention includes a method of embolization. In this method at least one compressible embolization particle is urged through a catheter and positioned in a target region of a blood vessel. The particle is in a compressed state while being urged through the catheter and expands to an expanded state upon exiting the catheter.

In another embolization method a first embolization device is positioned in a target region of a blood vessel. A second embolization device is then positioned in the blood vessel in close proximity to the first embolization device. At least one of the embolization devices is a compressible embolization particle as described herein.

The invention also includes a method of making a compressible embolization particle. The method includes mixing a polymer, such as PVA, a crosslinking agent, a gas and optionally a porogen to form the foam. The foam is then placed in a spherical mold having a diameter that corresponds to the desired diameter of the compressible embolization particle when hydrated for use. After curing, the particle is removed from the mold and the porogen is dissolved and separated from the particle to produce the embolization particle. In some situations, porogen is hydrolyzed in which case it is removed by rinsing.

BRIEF DESCRIPTION OF THE DRAWINGS

FIG. 3A shows a substantially spherical porous particle at 80× magnification having surface pores. Some interior pores can also be seen. An annular ring can be seen encircling the "equator" of the particle. FIG. 3B is a close up (300× magnification) of the surface of the north central hemisphere of the particles in FIG. 3A. FIG. 3C depicts a cross section of a dehydrated PVA compressible particle at 80× magnification.

DETAILED DESCRIPTION

One problem with the larger embolization particles in the prior art is that they require larger catheters for delivery to the patient. However, the compressibility of the particles of the present invention eliminates the need for larger catheters, making it possible to deliver relatively large particles through small catheters. Further, smaller particles of the present invention are also beneficial because such particles can be used with smaller catheters for delivery.

The compressible particles can be used in the creation of an artificial embolism that can be used to treat aneurysms, tumors, bleeding, vascular malformations, or otherwise be used to block blood flow to undesired areas by occluding blood vessels. According to one embodiment, the device is a dry, dehydrated substantially spherical particle of biocompatible polyvinyl alcohol ("PVA") foam material that when hydrated is compressible from its original hydrated volume to a constrained or smaller volume that can subsequently expand back toward the original volume. This compressibility allows the particle to be compressed in a delivery catheter having a diameter that is smaller than the diameter of the hydrated and expanded particle.

For purposes of this application, "compressibility" is defined as the ratio of the amount of the diameter of the particle that has been compressed to the total diameter of the particle in its fully expanded state. For example, a particle that has a diameter of 4 mm in its fully expanded state that can be compressed to 1 mm has a structural compressibility of 75% (3 mm (the amount of the particle diameter that the particle was compressed) divided by 4 mm (the total diameter of the particle in its expanded state)=75%).

Depending on the choice of catheter internal lumen diameter and the diameter of the hydrated particle, the particle can be compressed to a diameter perpendicular to the catheter lumen that is about 5% to about 90%, about 25% to about 85%, and about 40% to about 80% of the diameter of the expanded particle. This does not include the annular ring, if present.

The compressed particle is delivered to a target region of a blood vessel by an embolization device comprising a catheter and the compressible particle. Prior to the embolization procedure, the compressible particle is placed in the catheter lumen in a compressed state. After ejection from the lumen, the particle expands to provide for mechanical fixation of the particle within the vascular area, thereby providing occlusion of the vascular area.

Figure 1:
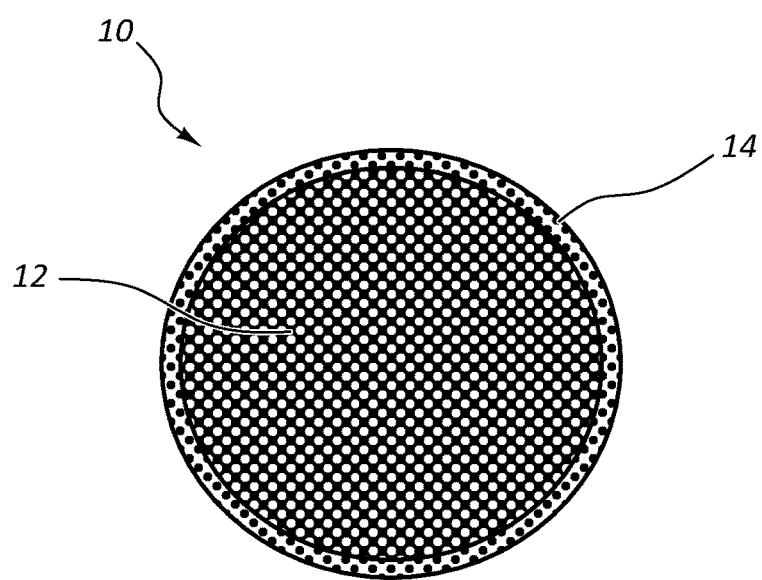
FIG. 1 is a cross-sectional view of a spherical polyvinyl alcohol foam embolization particle, according to one embodiment of the present invention.

FIG. 1 depicts an expandable embolization particle 10, according to one embodiment of the present invention. Particle 10 is preferably made of expandable PVA foam material and has a compressible, porous, spherical structure. In one aspect, the expandable material is formalin crosslinked PVA foam. Alternatively, the particle 10 can be made of polyurethane. In another aspect of the invention, the particle 10 can have any shape with a circular profile configured to provide a sealed occlusion with respect to the blood vessel in which it is positioned. For example, the particle 10 according to one embodiment can be cylindrical.

The particle 10 has an interior or inner portion 12 and an exterior layer 14 (also referred to as an "exterior portion" or "skin"). The interior portion 12 is more porous and contains pores with a larger diameter in comparison to the pores present in the skin 14. According to one embodiment, the pores in the exterior layer 14 have a diameter that is generally smaller than the diameter of the pores found the interior portion 12. In other words, the exterior layer 14 pores have a diameter that is generally smaller than the diameter of the pores found in the interior portion 12 of the particle. According to one embodiment, the pores in the interior portion of the particle are "macropores" having diameters of 10, 25, 50, 100, 200, 300, 400 or 500 microns or more. In some embodiments, the skin 14 has fewer pores, fewer and smaller pores, or no pores in comparison to the interior portion.

In a further aspect of the invention, at least a portion of the pores of the interior portion are interconnected. "Interconnected pores" (also referred to as "open pores") as used in the present application refers to pores that are in fluid communication within a solid material. The interconnected pores define an open, interconnected architecture of volume elements within the particle that can contain liquid in the hydrated state or gas in a dehydrated state.

The particles of the present invention are substantially spherical. The term "substantially spherical" as used herein refers to a generally spherical shape having a maximum diameter/minimum diameter ratio of from about 1.0 to about 2.0, more preferably from about 1.0 to about 1.5, and most preferably from about 1.0 to about 1.2. This definition is intended to include true spherical shapes and ellipsoidal shapes, along with any other shapes that are encompassed within the maximum diameter/minimum diameter ratio.

Figure 3A:
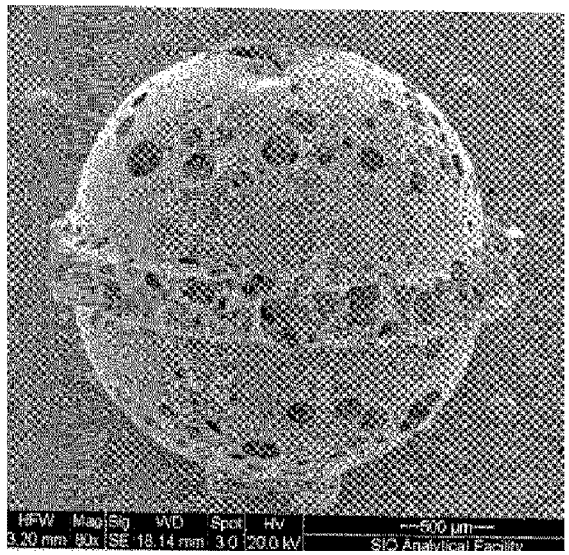
FIGS. 3A, 3B and 3C are Scanning Electron Micrographs (SEM's) of a dehydrated PVA particle made according to the invention.
Figure 3B:
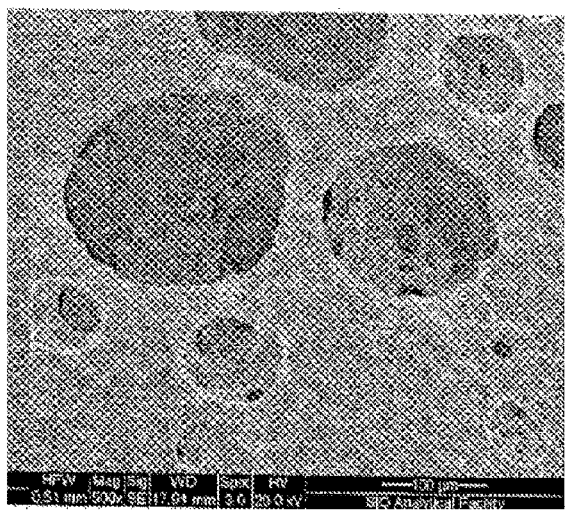
Figure 3C:
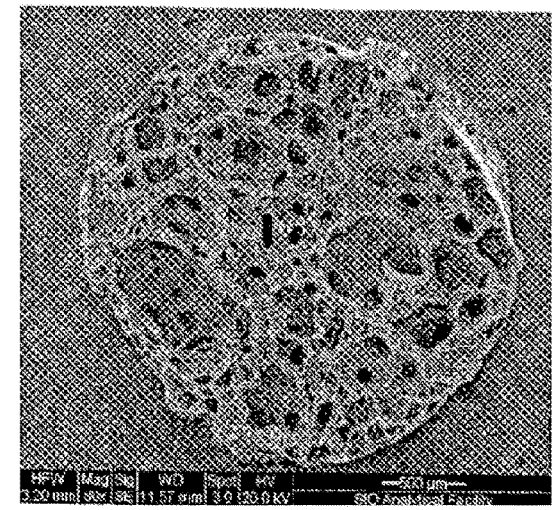

FIGS. 3A, 3B and 3C are scanning electron micrographs (SEM's) of a dehydrated PVA particle made according to the invention. FIG. 3A shows a substantially spherical porous particle at 80× magnification having surface pores. Some interior pores can also be seen. An annular ring can be seen encircling the "equator" of the particle. The annular ring is an artifact formed during curing in the joint between the two halves of the mold used to make the particle. The ring can be of any desired diameter by using a die to trim the ring before particle removal from one of the half molds. The annular ring is believed to impart additional stability to embolisms formed from the particles.

FIG. 3B is a close up (300× magnification) of the surface of the north central hemisphere of the particles in FIG. 3A. Interior pores can be readily seen. Some of the surface pores have diameters as large as about 50 microns with some having diameters as large as 100 or more microns. FIG. 3C depicts a cross section of a dehydrated PVA compressible particle at 80× magnification. The interior has some pores having a diameter from 100 to 500 microns with many of the pores having a diameter less than about 100 micron. The minimum pore size is about 1 micron.

The exterior layer 14 in FIG. 1 is an outer skin that provides increased structural strength, thereby reducing risk of fragmentation. Further, the exterior layer 14 can provide reduced friction when the exterior layer 14 contacts objects such as the interior portions of delivery systems during use. Such a strong exterior layer 14 with reduced exterior friction can aid in insertion into a blood vessel and reduce risk of recannalization and further, unintended embolization caused by debris that may be trapped in the larger inner pores. In one aspect of the invention, the relatively fewer, smaller, or lack of pores in the skin 14 enhance the structural strength and friction reducing characteristics of the skin 14. The structural strength of the skin results in a particle exhibiting much greater compressive size reduction by allowing for an interior portion having larger, more compressible pores and a foam with memory, wherein "memory" refers to the capacity of the particle to recover toward its original shape after deformation (elastic recovery). That is, the particle has memory because it can be compressed to a smaller diameter and upon release of the compressive force will return toward its original non-compressed diameter.

The particles of the present invention can be produced in the following manner. According to one embodiment, a PVA solution is mixed with a porogen. The amount of PVA in solution prior to mixing is preferably about 21%. Alternatively, the amount of PVA in solution can range from about 5% to about 24%.

The term "porogen" refers to a pore forming material dispersed in the polymer solution and subsequently removed to yield pores, voids, or free volume in the material. According to one embodiment, the porogen is starch that can be solubilized after particle formation. Alternatively, the porogen can be, but is not limited to, carbon dioxide, polyethylene glycol, or any of the inert gases.

After the PVA and porogen are mixed, a crosslinking component and crosslinking catalyst are added. The crosslinking component can be formaldehyde and the catalyst can be hydrochloric acid. Alternatively, the catalyst can be an acid such as sulfuric acid or, in a further alternative, almost any known mineral acid.

After the crosslinking component and catalyst are added to the mixture, air or any other inert gas is then added or "whipped" into the mixture to create a foam. The air is preferably added to the mixture using a high speed mixer. A single element egg beater in a high speed air motor (7,000±400 rpm) can be used to make the foam before the mixture has cross linked to any significant degree. The mixing continues until the mixture stops expanding. According to one embodiment, the foam stops expanding after about 30 seconds of mixing. Alternatively, the mixing period lasts for from about 5 seconds to about 4 minutes. In a further alternative, the mixing period lasts for from about 10 seconds to about 1 minute.

Subsequently, the reaction mixture of PVA, porogen, and air is placed into a mold and heated for about five hours. Alternatively, the mixture is heated for a period of time ranging from about three hours to about ten hours. In a further alternative, the mixture is heated for a period of time ranging from about 4 hours to about 7 hours. It is understood that crosslinking begins to occur after the addition of the crosslinking component and the crosslinking catalyst such that the resulting product removed from the mold comprises crosslinked PVA.

The mold, according to one embodiment, is a polypropylene mold defining a substantially spherical void, thereby producing a substantially spherical particle. Of course, this definition is intended to include true spherical shapes and ellipsoidal shapes, along with any other shapes that are encompassed within the maximum diameter/minimum diameter ratio.

The reaction mixture is injected into the spherical void. The mold, in accordance with one embodiment, has a bleed hole in communication with the spherical void to allow for excess mixture to drain from the void as necessary. According to one embodiment, the mixture is injected using a syringe. In one embodiment, a volume of the mixture greater than the volume of the void is injected such that the portions of the mixture in contact with the mold are compressed or placed under pressure, thereby forcing some portion of the mixture to escape through the bleed hole. The compression or pressure placed upon the exterior portions of the mixture ensures that the entire void is filled with mixture and that the mixture contacts all or substantially all of the surface of the mold defining the void, thereby ensuring a smooth skin or surface to the resulting particle that can contain pores or a relatively nonporous skin. According to one embodiment, the polypropylene in the mold further enhances the smooth-even, in some cases, glossed-finish of the resulting particle. The resulting particle consists of an interior portion having larger pores as a result of the relatively unconstrained, non-compressed formation away from the surface of the mold and an exterior layer or skin that is compacted, relatively smooth, and finished as a result of the compression on those areas of the mixture caused by contact with the mold, though one or more macropores may be present in the skin.

In one aspect of the invention, the mold has two components, both of which define a hemispherical void. In this embodiment, the reaction mixture is injected into both voids in excess such that when the two molds are coupled to define a spherical void, the mixture is compressed or pressured in the void and the excess mixture is forced out of the bleed hole in communication with the void. Again, the result of the compression or pressure is a particle with a relatively nonporous or microporous skin or surface with a substantially smooth finish.

In use, a particle or particles of the present invention can be positioned in a target region of a blood vessel to occlude the vessel. According to one embodiment, the method includes delivery of the particle to the target region with a delivery system.

Prior to delivery of the particle, according to one embodiment of the present invention, the user or physician can perform angiography to determine the vascular supply to the target area. Further, the resulting angiogram can be used to determine the appropriate route for delivery system insertion.

In accordance with another embodiment, another pre-delivery step is hydration of the embolization particle. The particle is hydrated by adding hydration fluid to the particle in a container—or placing the particle in an amount of hydration fluid in a container. Optionally, the particle may be compressed while it is in the fluid. As the particle expands from its compressed state to its expanded state, hydration fluid is drawn into the voids or pores in the interior portions of the particle, thereby accelerating hydration of the particle. According to one embodiment, this hydration process can be performed in a period of about 5 seconds. Alternatively, the process can be performed in a period ranging from about 2 seconds to about 10 seconds. The hydration fluid is any known fluid for hydrating embolization particles including contrast agent, saline, or any combination thereof, where it is understood that the term "saline" encompasses any salt solution acceptable for physiological use. It is understood that hydration fluid, may contain contrast agent or may be a contrast agent. For example, the hydration fluid can be a contrast agent such as Oxilan 300®.

Delivery of the particle, according to one embodiment, includes positioning the delivery system such that the system is in fluid communication with the target area of the blood vessel. In one aspect of the invention, the delivery system comprises a catheter.

The delivery process further includes placing a compressible embolization particle into a lumen of the delivery system. In one aspect of the invention, the diameter of the particle in its expanded state is greater than the inner diameter of the lumen of the delivery system such that the particle is in a compressed state in the lumen.

Figure 2:
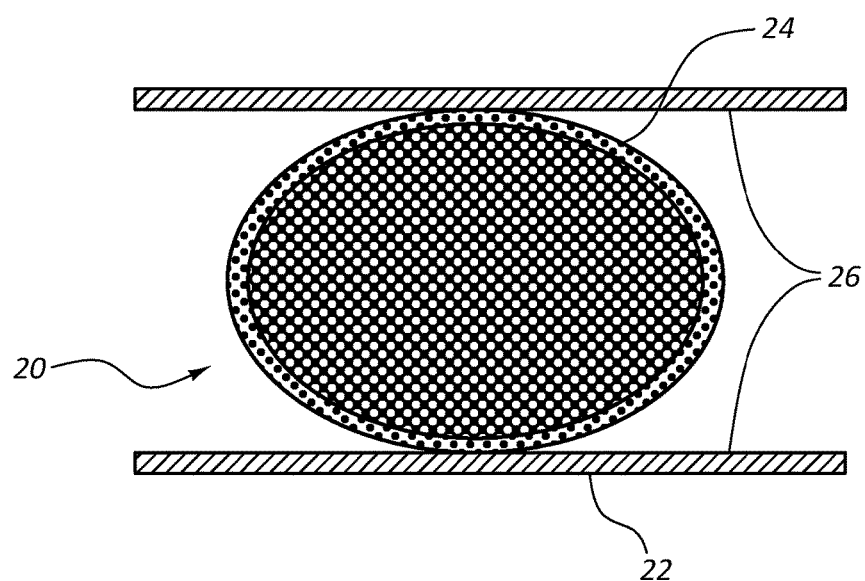
FIG. 2 is a cross-sectional view of a spherical polyvinyl alcohol foam embolization particle, according to another embodiment of the present invention.

The particle is then delivered to the target region by ejecting or expelling the particle from the lumen of the delivery system. Upon exit from the lumen into the target area, the particle expands from its compressed state toward its expanded state. As depicted in FIG. 2, the particle 20 is configured such that the diameter of the target region of the blood vessel 22 is greater than the diameter of the lumen but less than the diameter of the particle 20 in its fully expanded state such that the particle 20 upon exiting the delivery system expands until the exterior 24 of the particle 20 contacts the inner wall 26 of the vessel 22. In one aspect of the invention, the diameter of the vessel 22 as described above results in the particle 20 being in a compressed state (though not as compressed as in the lumen of the delivery system), thus resulting in the particle 20 exerting a continuous outward pressure on the inner wall 26 of the blood vessel. This pressured contact between the particle 20 and the blood vessel 22 can help to stabilize the particle 20 in a single position within the target area of the blood vessel 22, thereby resulting in occlusion of the vessel 22. According to one embodiment, the pressured contact works to retain the particle 20 in the single position in the vessel 22 such that a substantial force is required to move the particle 20. Alternatively, the pressured contact results in the substantial mechanical fixation of the particle 20 in a single position in the blood vessel 22. In one embodiment, additional mechanical fixation occurs as a result of the blood clotting caused by the presence of the particle and by the PVA material, and further occurs as a result of the subsequent healing process. The blood clotting forms on both sides of the particle or at least downstream of the particle, thereby providing further mechanical fixation. Further, during the healing process, the immune system of the human body recognizes that the particle is a foreign object and attempts to form tissue around the particle, thereby providing further mechanical fixation.

According to one embodiment, the first step in delivering the particle of the present invention to the target region is positioning a catheter in a patient such that the distal end of the catheter is located at or near the target region in the patient's blood vessel. In one alternative embodiment, the catheter has a stopcock at the proximal end of the catheter configured to close off the catheter to prevent loss of blood through the catheter prior to delivery of a particle of the present invention through the catheter. In another alternative, a stopcock is placed on the proximal end of the catheter after the catheter is positioned in the patient to prevent blood loss through the catheter.

Once the catheter is positioned appropriately, the embolization particle of the present invention is positioned in the connection portion of the catheter (not shown), which is located at the proximal end of the catheter. According to one embodiment, the connection portion of the catheter is a luer connector hub such that the particle is positioned in the connector hub. Alternatively, in embodiments in which a stopcock is positioned on the proximal end of the catheter as described above, the connection portion of the catheter is the stopcock.

The particle of the present invention, in one aspect of the invention, has a diameter that is smaller than the inner diameter of the connection portion of the catheter but larger than the inner diameter of the catheter lumen such that the particle is easily positioned in the hub but requires force to be urged into the catheter lumen. The next step, therefore, is to urge the particle from the luer connector hub into the catheter lumen. According to one embodiment, the particle is urged into the catheter lumen using a syringe containing hydration fluid. That is, with the particle positioned in the connector hub of the catheter, a syringe is connected with the hub, thereby locking or enclosing the particle into the connection between the hub and the syringe. The plunger of the syringe is then depressed, providing a hydraulic force that moves the particle into the catheter lumen.

According to one embodiment, the particle is then urged along the catheter lumen and urged out of the catheter and into the target region using a blunt-ended guidewire. The syringe used to load the particle into the lumen is removed from the catheter. It is possible to remove the syringe without blood loss through the catheter because the particle, having in its expanded state a larger diameter than the lumen of the catheter, has sealed the lumen of the catheter. Once the syringe is removed, a guidewire is inserted into the proximal portion of the catheter and contacts the particle, urging it toward and ultimately out of the distal end of the catheter and into the target region of the patient's blood vessel.

Figure 4:
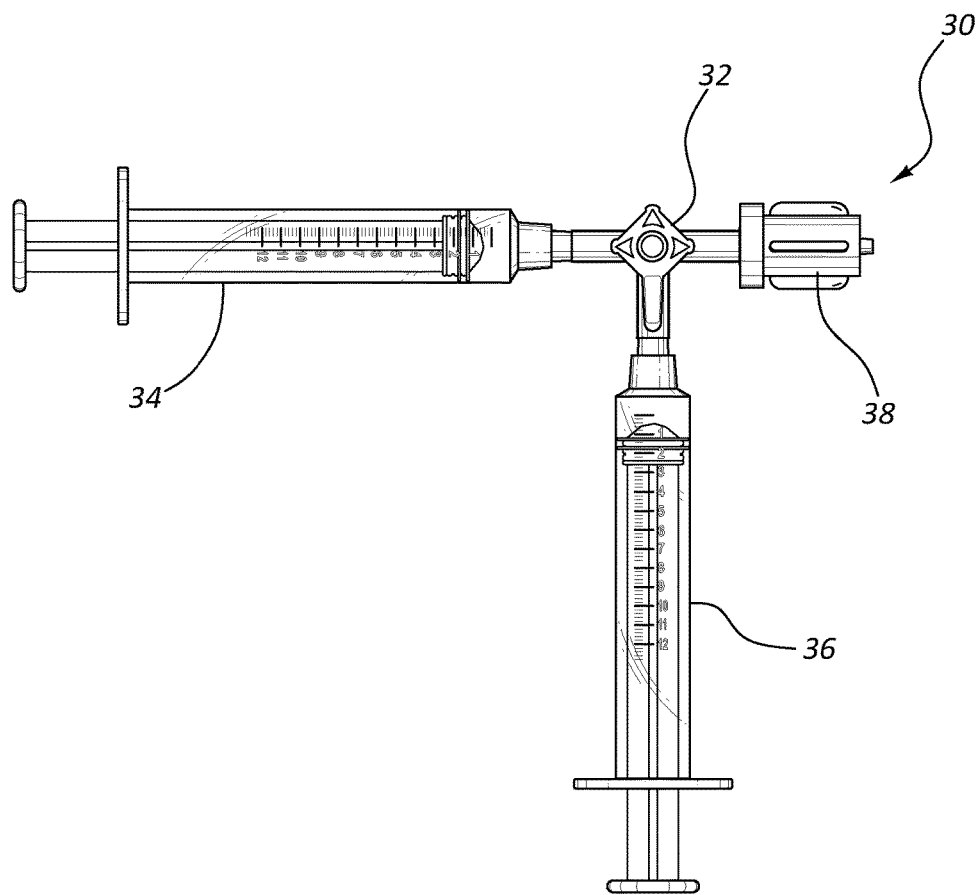
FIG. 4 is a side view of a delivery system, according to one embodiment of the present invention.
Figure 5:
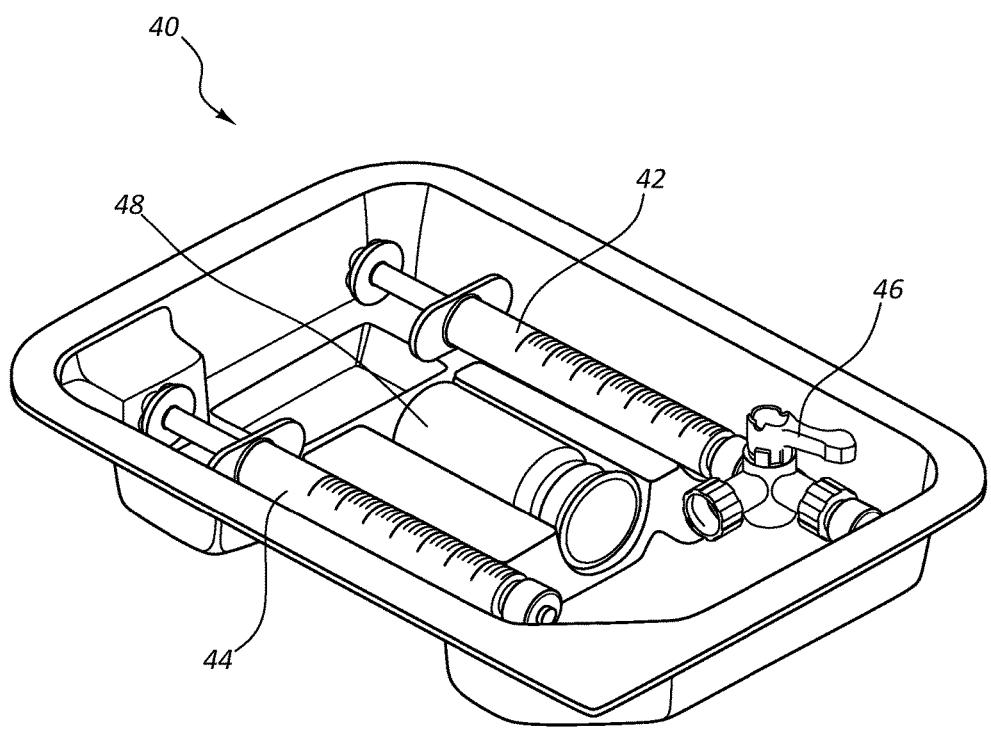
FIG. 5 is a perspective view of a kit containing a delivery system and an embolization particle, according to one embodiment of the present invention.

Alternatively, the particle can be delivered using a delivery system instead of a guidewire. FIG. 4 depicts a delivery system or device 30, according to one embodiment of the present invention. The device 30 has a connection component 32 which, in this embodiment, is a three-way stopcock. The coupling portion 38 of the connection component 32 is coupled to a catheter (not shown). Syringes 34 and 36 are coupled to the stopcock 32. FIG. 5 depicts an alternative embodiment in which the delivery system is provided as a kit 40. The kit 40 includes two syringes 42 and 44, a connection component 46, and a vial 48 containing at least one embolization particle.

Using the delivery system 30 of FIG. 4 for exemplary purposes, the delivery system 30 can be used in the following manner, according to one embodiment of the present invention. First, as described above, the embolization particle is positioned in the connection portion of the catheter. With the particle positioned in the hub, the coupling portion 38 of the connection component 32 of the delivery device 30 is coupled to the luer connection hub of the catheter (not shown), thereby enclosing the embolization particle within the connection between the coupling portion 38 and the luer connection hub of the catheter (not shown).

According to one embodiment, one of the two syringes 34 or 36 contains hydration fluid and the other of the two syringes 34 or 36 is empty. For purposes of this example, syringe 36 is a 1 ml syringe that contains hydration fluid, while syringe 34 is empty. However, according to another embodiment, syringe 36 is empty and syringe 34 contains hydration fluid. With the particle positioned within the coupling space of the coupling portion 38 and the catheter luer connection hub (not shown), the stopcock 32 is adjusted such that the syringe 36 is in fluid communication with the syringe 34 and a small amount of hydration fluid is transferred from the syringe 36 to the empty syringe 34. According to one embodiment, 0.1 ml of hydration fluid is transferred to the syringe 34. Alternatively, any small amount ranging from about 0.05 ml to about 1.0 ml can be transferred. Alternatively, an amount of hydration fluid ranging from about 0.1 ml to about 0.5 ml can be transferred. The stopcock 32 is then adjusted such that the syringe 34 is in fluid communication with only the catheter lumen. With the syringe 34 in fluid communication with the catheter lumen, the user injects the small amount of hydration fluid from the syringe 34 into the catheter, thereby loading the particle into the catheter lumen. According to one embodiment, the user pushes the plunger of syringe 34 quickly and forcefully, thereby urging the particle into the lumen. In one alternative embodiment, the step of transferring a small amount of hydration fluid to the syringe 34 and then forcefully injecting the small amount into the catheter, thereby loading the particle, can be repeated once or twice to insure loading of the particle.

Once the particle is positioned within the catheter lumen, the particle is urged through the catheter using a syringe containing hydration fluid. According to one embodiment, syringe 34 is used to urge the particle along the catheter. Alternatively, the stopcock 32 can be adjusted such that syringe 36 containing hydration fluid is in fluid communication with the catheter lumen and syringe 36 can be used to urge the particle along the catheter. In a further alternative, the delivery device 30 is removed from the catheter and another, separate syringe containing hydration fluid is connected to the catheter and used to urge the particle through the catheter. Alternatively, a guidewire is used to urge the particle through the catheter.

According to an alternative embodiment, the present invention relates to a supplemental occlusion particle configured to enhance the treatment of aneurysms, tumors, bleeding, and otherwise completely block blood flow to undesired anatomical areas by supplementing the occlusion of blood vessels. This embodiment of the invention relates to the introduction of a secondary, supplemental compressible embolic device into a target area of a blood vessel to compliment the action of one or more primary embolic devices or materials. Such primary embolic devices can be smaller embolization particles such as Microstat™ (Surgical Corporation); Contour SE™ (Boston Scientific Corporation), Embosphere™ (Biosphere Medical Inc.) or Bead Block™ (Biocompatables International Plc), embolization coils, or liquid polymer embolization systems which cure in vivo.

Figure 6:
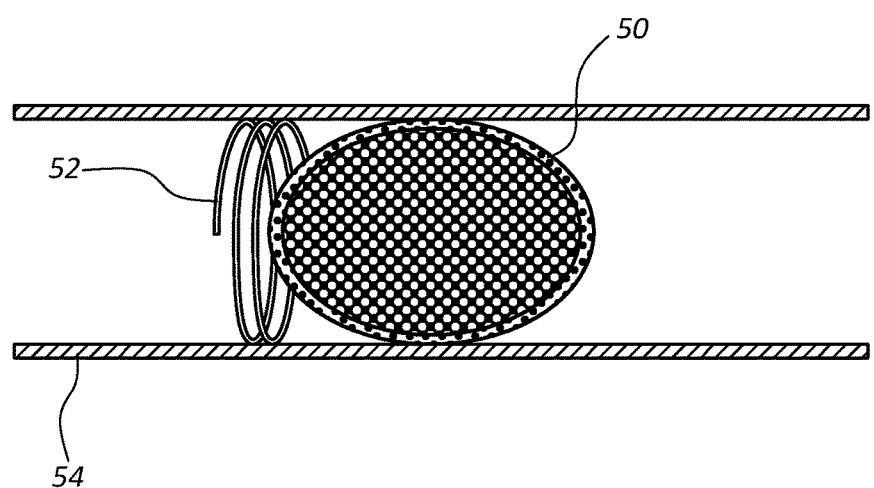
FIG. 6 is a side view of a supplemental embolization particle positioned in a blood vessel in conjunction with an embolization coil, according to one embodiment of the present invention.

FIG. 6 depicts a supplemental occlusion particle 50, according to an alternative embodiment of the present invention. The particle 50 is positioned to operate in conjunction with the embolization coil 52 to provide occlusion of the blood vessel 54. The particle 50 is configured to expand from a compressed state having a first volume to an expanded state having a second, relatively larger volume in comparison with the first. According to one embodiment, the particle 50 is configured to expand within the vessel 54 and thereby provide a degree of blood-flow-blocking mechanical fixation to support or enhance the embolic action of the primary device 52. According to one embodiment, the use of the supplemental particle 50 in cooperation with a primary embolization device such as the coil 52 results in complete or substantially complete occlusion and reduces or even eliminates the risk of recanalization.

Figure 7:
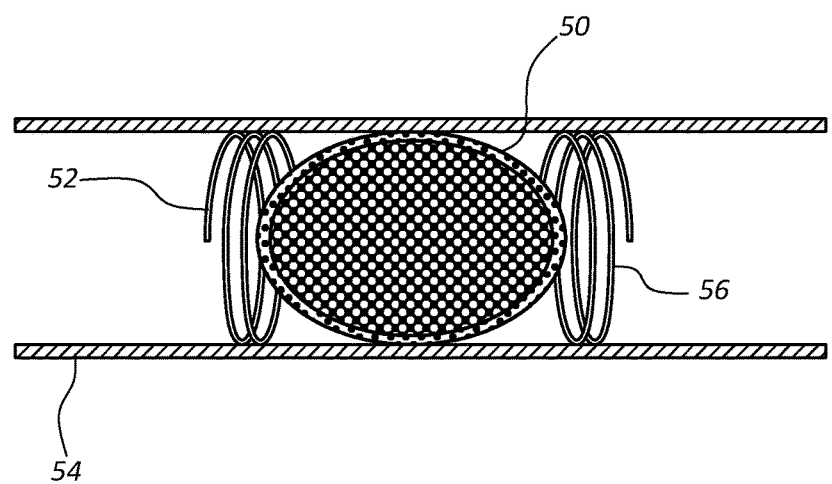
FIG. 7 is a side view of a supplemental embolization particle positioned in a blood vessel in conjunction with two embolization coils, according to one embodiment of the present invention.
Figure 8:
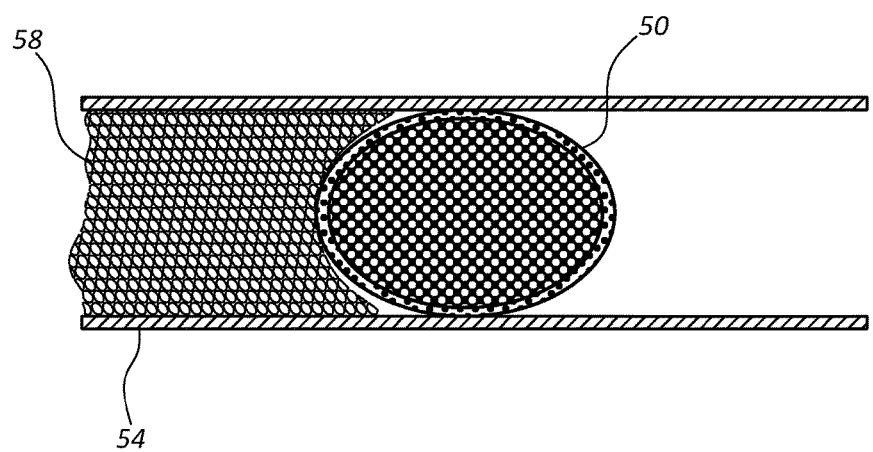
FIG. 8 is a side view of a supplemental embolization particle positioned in a blood vessel in conjunction with embolization particles, according to one embodiment of the present invention.

In an alternative embodiment as depicted in FIG. 7, the particle 50 is positioned to operate in conjunction with two embolization coils 52 and 56 to provide occlusion. As shown in yet another alternative embodiment in FIG. 8, the particle 50 can also be used in conjunction with smaller embolization particles 58 or any other known embolization device.

The supplemental occlusion particle 50, in accordance with one aspect of the invention, is an embolic PVA particle as described above and depicted in FIG. 1, having an inner, porous portion and an outer layer comprised of fewer and/or closed pores having an average diameter that is smaller than the average diameter of the pores in the inner portion of the particle. Alternatively, the supplemental occlusion particle 50 is any embolic device having materials with a highly compressible porous structure, such as crosslinked PVA foams. In a further alternative, the PVA foam can also be configured radiopaque by a variety of well known methods. In yet another alternative, the supplemental occlusion particle can be any known embolic particle or device capable of expanding radially inside the vessel and thereby providing a degree of mechanical fixation to support the blocking action of the primary embolization device to provide complete and permanent occlusion of the vessel.

In use, the supplemental particle can operate in the following manner. According to one embodiment, the supplemental particle is positioned in operable proximity to the primary occlusion device. That is, the supplemental particle is positioned in a location such that it operates to enhance the degree of blood-flow blockage created by the primary device. The supplemental particle is positioned using a delivery method or system. According to one embodiment, the particle is positioned using a guidewire as described herein. Alternatively, the particle is positioned using one of the systems depicted in FIG. 4 or 5 or a similar system. The delivery system is positioned with respect to the target area of the blood vessel to allow for positioning the particle in the target area. The particle is placed in the lumen of the delivery system which, according to one embodiment, is a catheter. The lumen has a smaller inner diameter than the diameter of the particle in its expanded state. As such, the particle is retained in a compressed state by the lumen. The particle is then expelled or ejected from the lumen of the delivery device into the blood vessel at the target area such that it is positioned in operable proximity with the primary device. Upon or during exit from the lumen, the supplemental particle expands in the blood vessel.

Tables I-VI compare the compressibility and catheter compatibility of Embosphere™ particles (Tables I and II), Contour SE™ particles (Tables III and IV) and Maxistat™ particles (which are within the scope of the invention) (Tables V and VI).

Although the present invention has been described with reference to preferred embodiments, persons skilled in the art will recognize that changes may be made in form and detail without departing from the spirit and scope of the invention.

TABLE I

CATHETER COMPATIBILITY OF EMBOSPHERE MICROSPHERES

| From Their Catheter Compatability Chart | | | Embosphere Microspheres (microns) | | | | | |
|---|---|---|---|---|---|---|---|---|
| Catheter ID (inches) | Catheters | MFG | 40-120 | 100-300 | 300-500 | 500-700 | 700-900 | 900-1200 |
| 0.035-0.038 | All 4Fr and 5F | | X | X | X | X | X | X |
| 0.028 | EmboCath | BioSphere | X | X | X | X | X | |
| 0.024-0.027 | | Terumo | | | | | | |
| | Progreat | Bost Sci | | | | | | |
| | FasTracker-325 | Bost Sci | | | | | | |
| | Renegade Hi-Flo | Cordis | X | X | X | X | X | |
| | Mass Transit | Micro | | | | | | |
| | Rebar-027 | Ther | | | | | | |
| 0.019-0.023 | RapidTransit | Cordis | | | | | | |
| | Renegade | Bost Sci | X | X | X | X | | |
| | Turbo Tracker-18 | Bost Sci | | | | | | |
| 0.014-0.018 | Regatta | Cordis | | | | | | |
| | Prowler-10 | Cordis | X | X | X | | | |
| | Prowler-14 | Cordis | | | | | | |
| | Tracker Excel-14 | Bost Sci | | | | | | |
| 0.008-0.130 | Spinnaker Elite 1.5 | Bost Sci | | | | | | |
| | Spinnaker Elite 1.8 | Bost Sci | X | X | | | | |
| | Magic 1.5 | Balt | | | | | | |

TABLE II

COMPRESSIBILITY OF EMBOSPHERE MICROSPHERES
EMBOSPHERE

| High End of Particle Range in Microns | High End of Particle Range in Inches | Embosphere Compatible Smallest ID Size (Inches) | Compression[1] |
|---|---|---|---|
| 300 | 0.011811 | 0.008 | 32.3% |
| 500 | 0.019685 | 0.014 | 28.9% |
| 700 | 0.027559 | 0.019 | 31.1% |
| 900 | 0.035433 | 0.024 | 32.3% |
| 1200 | 0.047244 | 0.035 | 25.9% |

[1]Embosphere Catheter Compatibility Chart states up to 33% compression

TABLE III

CATHETER COMPATIBILITY OF CONTOUR MICROSPHERES

| From Their Catheter Compatability Chart | | | Contour SE Microspheres (microns) | | | | |
|---|---|---|---|---|---|---|---|
| Catheter ID | Including Catheters | MFG | 100-300 | 300-500 | 500-700 | 700-900 | 900-1200 |
| 0.038 | Selective 4Fr and 5F | Bost Sci | X | X | X | X | X |
| 0.024 | FasTracker-325 Renegade Hi-Flo | Bost Sci | X | X | X | X | |
| 0.021 | Renegade-18 | Bost Sci | X | X | X | | |
| 0.013 | Excelisor SL-10 | Bost Sci | X | X | | | |
| 0.011 | Spinnaker Elite 1.5Fr | Bost Sci | X | | | | |

TABLE IV

COMPRESSIBILITY OF CONTOUR SE PARTICLES CONTOUR SE

| High End of Particle Range in Microns | High End of Particle Range in Inches | Contour SE Compatible Smallest ID Size (Inches) | Compression |
|---|---|---|---|
| 300 | 0.011811 | 0.011 | 6.9% |
| 500 | 0.019685 | 0.013 | 34.0% |
| 700 | 0.027559 | 0.021 | 23.8% |
| 900 | 0.035433 | 0.024 | 32.3% |
| 1200 | 0.047244 | 0.038 | 19.6% |

TABLE V

Compressibility of Surgica Maxistat Particles[1]

| Product | Hydrated Particle Size (microns) | Particle Size in Inches | Catheter Smallest ID Size (Inches) | Compression | MaxiStat Dehydrated Particles Size Range in Microns | | Mean | Calculated % Swelling upon Hydration in saline |
|---|---|---|---|---|---|---|---|---|
| MaxiStat 2500 | 2500 | 0.098425 | 0.027 | 72.6% | 1875 | 2250 | 2062.5 | 21.2% |
| MaxiStat 3000 | 3000 | 0.11811 | 0.035 | 70.4% | 2250 | 2625 | 2437.5 | 23.1% |
| MaxiStat 3500 | 3500 | 0.137795 | 0.035 | 74.6% | 2625 | 2800 | 2712.5 | 29.0% |
| MaxiStat 4000 | 4000 | 0.15748 | 0.035 | 77.8% | 2800 | 3200 | 3000 | 33.3% |

[1]The MaxiStat particles are substantially spherical porous embolization particles made by Surgica Corporation (El Dorado Hills, CA)

TABLE VI

| | | | MaxiStat ™ PVA Foam Embolization Particles (microns) | | | |
|---|---|---|---|---|---|---|
| Catheter ID | Catheters | MFG | 1,875-2,250 | 2,250-2,625 | 2,625-2,800 | 2,800-3,200 |
| 0.038 | Soft-Vu Simmons-"Sidewinder" ST | AngioDynamics | X | X | X | X |
| 0.035 | Mariner Hydrophilic Coated Simmons-"Sidewinder" | AngioDynamics | X | X | X | X |
| 0.027 | Slip-Cath Infusion Catheter | Cook | X | | | |

EXAMPLES

Example 1

A crosslinked PVA embolization particle was prepared in the following manner. A mixture of 26.2 grams of PVA and 98.9 grams of deionized water was rapidly heated to 100° C. and held for 12 minutes. Subsequently, 39.9 grams of the resulting PVA solution was transferred for reaction purposes into a reaction kettle (a glass beaker) and set aside and allowed to cool. Separately, a mixture of 15 grams of rice starch and 135 grams of deionized water was heated to 80° C. and then 9.5 grams of the material was added to the PVA solution and thoroughly mixed. To this resulting mixture was added 3.6 grams of concentrated hydrochloric acid and 6.4 grams of about 37% formaldehyde (formalin solution) to form the reaction solution.

The reaction solution was then placed in a 2 liter glass reaction kettle and mixed at about 7000 rpm with a high-speed mixer having a high-speed air motor and using a mixing blade to whip air into the mixture until the foam stopped expanding and the resulting mixture achieved an appearance similar to whipped cream, which required about 30 seconds of mixing. The mixing blade was similar in configuration to an egg beater.

After mixing, the reaction mixture was transferred to spherical molds of 2.5 mm, 3.0 mm, 3.5 mm and 4.0 mm diameter and allowed to cure for 5 hours at 55° C. The polypropylene molds used in this example have two identical 1 inch by 1 inch square pieces that are 0.2 inches in thickness. Each piece defines a hemisphere on one side, wherein the hemisphere is sized according to the desired size of the embolization particle. Further, each piece also defines a 0.039 inch bleed hole in fluid communication with the hemisphere, thereby allowing relief of any overfill amount through the bleed hole.

The resulting products were partially acetalized cross-linked PVA sponges, which were then thoroughly washed to remove excess formaldehyde and hydrochloric acid. Certain portions of the resulting sponges were then removed, including the center ring and the poles (flashing), to create substantially spherical particles of 2.5 mm, 3.0 mm, 3.5 mm and 4.0 mm in diameter in their hydrated, fully expanded state. The sponges were then dried for 16.5 hours at 50° C. to complete the manufacturing process.

Example 2

The same procedure performed in Example 1 was repeated, but the formaldehyde additive was reduced to 5.2 grams. It was believed that the reduction in formaldehyde would change the pot-life of the reaction solution, wherein "pot-life" is intended to mean the useful life of the mixture (after some period of time, the mixture ages to the point that it cannot be used to create a particle of the present invention). However, no significant change in pot-life was observed.

Example 3

The same procedure performed in Example 1 was repeated, but the hydrochloric acid additive was reduced to 5.0 grams. The resulting sponges had both an increased firmness and increased resilience in comparison to the sponges produced in Example 1, wherein firmness is a qualitative measure of the compressibility of the particle. Further, the pot-life of the reaction material was decreased by about 30 seconds.

Example 4

The same procedure performed in Example 1 was repeated, but the hydrochloric acid additive was reduced to 2.1 grams. The resulting sponges had both a decreased firmness and decreased resilience in comparison to the sponges produced in Example 1 such that the resulting sponges in the present example were significantly less "sponge-like" in comparison to the sponges produced in Example 1.

Example 5

SEM Images

The instrument used was a Quanta 600 Environmental Scanning Electron Microscope manufactured by the FEI Company (Hillsboro, Oreg.) and available at the Scripps Institute of Oceanography (San Diego, Calif.).

All samples were prepared (methods well known in the art) by Critical Point Drying, exchanging 200 proof ethanol for the saline hydration fluid, then exchanging the ethanol with liquid CO2 (4×), then finally heating to drive the $CO^2$ off as a gas. The samples were then transferred to carbon tape and sputter coated with gold/palladium. The samples were then imaged under high vacuum SEM. FIGS. 3A-3C were made according to this protocol.

What is claimed is:

1. A method of embolization, comprising:
   positioning a substantially spherical particle in a target area of a blood vessel of a patient, the particle comprising:
      an interior portion and an exterior surface layer, wherein the interior portion extends from a center of the particle to the exterior surface layer, wherein the exterior surface layer extends around the interior portion and defines an exterior surface of the particle;
      wherein the interior portion comprises pores having diameters of 25 microns or more, wherein at least a portion of the pores are interconnected, wherein the exterior surface of the particle comprises surface pores having diameters of at least 50 microns, wherein the particle has a compressibility of from 60% to 95% and a diameter when hydrated and fully expanded that ranges from 1000 microns to 10000 microns;
      wherein the diameter when hydrated and fully expanded is greater than an inner diameter of the target area of the blood vessel; and
   occluding blood flow through the blood vessel with the particle.

2. The method of claim 1, further comprising:
   obtaining the particle, wherein the particle is in dehydrated form; and
   hydrating the particle by adding hydration fluid to the particle prior to positioning the particle in the target area of the blood vessel.

3. The method of claim 2, wherein the hydration fluid is a contrast agent, saline or any combination thereof.

4. The method of claim 1, wherein the diameter of the particle when fully expanded ranges from 2000 microns to 4500 microns.

5. The method of claim 1, wherein the interior of the particle comprises pores having diameters that are greater than 100 microns.

6. The method of claim 1, wherein the particle comprises a polyvinyl alcohol (PVA) polymer.

7. The method of claim 1, wherein the particle comprises polyurethane.

8. A method of embolization comprising:
   obtaining at least one substantially spherical particle comprising an interior portion comprising interior pores and an exterior portion comprising exterior pores, wherein at least a portion of the interior pores extend to the exterior pores, wherein the particle has a compressibility of from 60% to 95% and a diameter when hydrated and in a fully expanded state that ranges from 1000 microns to 10000 microns;
   urging the particle through a catheter, wherein the particle is in a compressed state while in the catheter;
   positioning the particle in a target vascular area, wherein upon exiting the catheter the particle expands until an exterior of the particle contacts an inner wall of the target vascular area, wherein a diameter of the target vascular area is less than the diameter of the particle in the fully expanded state such that the particle expands to a first expanded state that is less than the fully expanded state and exerts pressure on the inner wall of the target vascular area; and
   occluding blood flow through the target vascular area.

9. The method of claim 8, wherein urging the particle through the catheter comprises contacting the particle with a guidewire.

10. The method of claim 8, wherein urging the particle through the catheter comprises applying fluid pressure to the particle.

11. The method of claim 8, further comprising;
loading the particle into the catheter comprising:
positioning the particle in a luer hub of the catheter;
coupling a syringe containing hydration fluid to the luer hub; and
operating the syringe to urge the particle out of the luer hub and into the catheter.

12. The method of claim 8, further comprising:
loading the particle into the catheter comprising:
positioning the particle in a luer hub of the catheter;
coupling a three-way stopcock to the luer hub, wherein the stopcock is coupled to a first and second syringe, wherein one or both of the syringes initially contain hydration fluid; and
operating the first syringe to urge the particle out of the luer hub and into the catheter.

13. The method of claim 12, wherein urging the particle through the catheter comprises operating the second syringe.

14. The method of claim 8, wherein the particle in the first expanded state is substantially fixed in position in the target vascular area.

15. A method of embolization comprising:
positioning a first embolization device in a target vascular area;
positioning a second embolization device in proximity to the first embolization device; and
occluding blood flow through the vessel,
wherein the first embolization device comprises a first substantially spherical particle comprising interior pores; wherein at least a portion of the interior pores are interconnected, wherein the first particle has a compressibility of from 60% to 95% and a diameter when hydrated and fully expanded that ranges from 1000 microns to 10000 microns;
wherein the second embolization device comprises a second substantially spherical particle having a diameter when hydrated and fully expanded that ranges from 300 microns to 1200 microns and a compressibility of from 6.9% to 34%.

16. The method of claim 15, wherein the diameter of the first particle when fully expanded ranges from 2000 microns to 4500 microns.

17. The method of claim 15, wherein the interior cores of the first particle have diameters that are greater than 10 microns.

18. The method of claim 15, wherein the first particle comprises a polyvinyl alcohol (PVA) polymer.

* * * * *

UNITED STATES PATENT AND TRADEMARK OFFICE
CERTIFICATE OF CORRECTION

PATENT NO. : 10,448,955 B2  
APPLICATION NO. : 13/717452  
DATED : October 22, 2019  
INVENTOR(S) : Matson et al.

Page 1 of 1

It is certified that error appears in the above-identified patent and that said Letters Patent is hereby corrected as shown below:

In the Claims

Column 18, Line 22 reads, ". . . wherein the interior cores . . ." which should read, ". . . wherein the interior pores . . ."

Signed and Sealed this  
Thirty-first Day of December, 2019

Andrei Iancu  
*Director of the United States Patent and Trademark Office*